United States Patent [19]

Zakoshansky

[11] Patent Number: 5,254,751
[45] Date of Patent: Oct. 19, 1993

[54] METHOD FOR THE DECOMPOSITION OF CUMENE HYDROPEROXIDE BY ACIDIC CATALYST TO PHENOL AND ACETONE

[75] Inventor: Vladimir M. Zakoshansky, St. Petersburg, U.S.S.R.

[73] Assignee: General Electric Company, Pittsfield, Mass.

[21] Appl. No.: 944,688

[22] Filed: Sep. 14, 1992

[51] Int. Cl.$^5$ ............................................. C07C 37/08
[52] U.S. Cl. ................................... 568/798; 568/385
[58] Field of Search ................................ 568/385, 798

[56] References Cited

U.S. PATENT DOCUMENTS

4,358,618  11/1982  Sifniades et al. ............... 568/798

FOREIGN PATENT DOCUMENTS

| 537066 | 12/1972 | U.S.S.R. | 568/385 |
| 629429 | 9/1949 | United Kingdom | 568/798 |
| 864486 | 4/1961 | United Kingdom | 568/798 |
| 1202687 | 8/1970 | United Kingdom | 568/798 |

*Primary Examiner*—Werren B. Lone

[57] ABSTRACT

A method for the enhanced decomposition of cumene hydroperoxide by acidic catalyst to phenol and acetone which comprises decomposing cumene hydroperoxide in a non-isothermal manner in the presence of excess acetone whereby the molar ratio of acetone to phenol in a decomposition reactor is from about 1.1:1 to 1.5:1.

A method for the selectivity of the decomposition of dicumyl peroxide to alpha methylstyrene also phenol and acetone in the presence of an acidic catalyst which comprises carrying out the decomposition at a temperature of from about 80° to 110° C.

A method for carrying out the decomposition of dicumyl peroxide with an acidic catalyst system which comprises performing such decomposition in the presence of the reaction product of (1) an amine with (2) an acidic material which can catalyze the decomposition of CHP.

A method for preparing phenol and acetone from the decomposition of CHP with an acidic catalyst which comprises (a) decomposing CHP at a specific acidic catalyst concentration and temperature thereby forming a composition comprising phenol, acetone and dicumyl peroxide, (b) transferring dicumyl peroxide to a plug flow reactor wherein decomposition of dicumyl peroxide to phenol acetone and AMS occurs at a lower acidic catalyst concentration and a higher temperature than the catalyst concentration and temperature in step (a).

A method for the decomposition of CHP and producing CHP decomposition products therefrom which comprises recycling the CHP decomposition products to a CHP feedstream in the quantity of from about 10-25 times the weight of the CHP feedstream.

39 Claims, 1 Drawing Sheet

METHOD FOR THE DECOMPOSITION OF CUMENE HYDROPEROXIDE BY ACIDIC CATALYST TO PHENOL AND ACETONE

BACKGROUND OF THE INVENTION

Phenol is manufactured commercially by several processes. However one of the key manufacturing processes is air oxidation of cumene to cumene hydroperoxide (CHP) followed by acid catalyzed cleavage of this CHP to phenol and acetone. The CHP decomposition is a very exothermic reaction which is normally carried out on a commercial scale in continuous stirred or back-mixed reactors. Generally in such reactors only a small fraction of CHP is unreacted at any given time and the reaction medium consists essentially of the products of decomposition of CHP, i.e. phenol and acetone plus any solvent for example, cumene, carried in the feed stream and other materials added with CHP to the reactor. Present in the feed stream to the cleavage reactor together with unreacted cumene and CHP are generally found small amounts of dimethylbenzyl alcohol (DMBA). Additionally small amounts of acetophenone (AP) are generally found as well. While the CHP is undergoing cleavage to phenol and acetone, the DMBA is also undergoing reaction to alphamethylstyrene (AMS), a useful product since it can be readily hydrogenated back to cumene. When reacted by itself under appropriate conditions DMBA can provide high yields of AMS. However in the presence of phenol and more specifically the mixture in the cleavage reactor, i.e. primarily phenol, acetone and cumene the usual AMS yield is normally about 50 to 60 mole % of the DMBA. Main by-products are AMS dimers and various cumylphenols which generally have no or very little commercial value in the relatively impure state as found in the cleavage reactor.

Generally the cleavage reaction has had very little study in the past. U.S. Pat. No. 4,358,618 issued to Allied, has reviewed the cleavage reaction to some extent. It also notes that the DMBA in the cumene oxidation product fed to the cleavage vessel will convert to AMS and other materials. However it found that the DMBA present in the cleavage reactor will react with CHP to form dicumylperoxide (DCP) and that such cleavage reaction should be carried out at a temperature between about 50° C. and about 90° C. wherein the CHP concentration is lowered to between about 0.5 and about 5.0 wt. % of the composition. This reaction product is then held at that temperature in a conduit for time sufficient to produce a second mixture wherein the CHP concentration is no more than about 0.4%. This new reaction mixture is then reacted at a very high temperature, generally between about 120° and about 150° C. under plug-flow reaction conditions to convert at least 90% of the DCP to AMS, phenol and acetone.

In this particular work, it is noted that the common cumene oxidation product is fed to the reactor. There is no indication of any recycle materials present in the reactor or any other increase in any specific concentrations of the materials normally present in the CHP feed stream. Additionally there is no particular control of the reaction temperatures nor is there any attempt to alter the concentration of the acid catalyst in the second and third steps, particularly the third step where the DCP is converted to AMS, phenol and acetone under high temperature.

This particular set of reactions is known to be kinetically fast and is generally run at a reasonably high temperature in order to obtain the fastest reaction, including the particularly high temperature of the conversion of DCP to AMS, phenol and acetone.

The cleavage reaction has been put through a detailed study. It has now been found that it is better to slow down the CHP decomposition reaction as well as the DCP decomposition reaction in order to achieve ultimately higher yields of phenol and acetone, primarily from the increased selectivity to AMS from the DCP decomposition. As stated previously AMS is then hydrogenated to cumene. When AMS selectivity is down, AMS dimers and what is generally known as tar are prepared to a much greater extent thereby decreasing the amount of useful AMS. In particular it has been found in the initial reaction wherein CHP is decomposed into phenol and acetone and DCP is made from the reaction of CHP and DMBA that the addition of recycle acetone as well as cumene has a particularly beneficial effect. It is preferable to do this mixing of the recycle stream prior to the entrance to the cleavage reactor. Such intense mixing brings about unusually better results. The actual CHP cleavage reaction initially stated is carried out in a non-isothermal manner and preferably in a multiplicity of sequential reactors, for example a shell-in-tube reactor, generally two to five reactors, particularly three, wherein temperature is maintained over a specific range for each reactor thereby obtaining optimal CHP conversion profile and yield. This entire first reaction is controlled by a plug-flow mini-reactor wherein the measurement of temperature difference at the inlet and outlet of the mini reactor is maintained in a certain range. This mini reactor is preferably installed as a by-pass on line at the product emitted from the last sequential reactor.

Additionally it has been observed that the preferred prior art DCP decomposition to AMS, phenol and acetone conducted at the higher temperatures of 120° C. to 150° C. is not truly realistic in a commercial phenol manufacturing process since it is subject to wide diversions from changes in manufacturing processing parameters such as the yield of AMS with respect to time. Also seemingly insignificant changes of CHP flow rate and concentration change in cleavage product composition both individually and together negatively affect the yield of AMS. In order to better control this decomposition reaction of DCP to phenol, acetone and AMS, I have lowered the temperature range substantially as well as decreased the quantity of strong acidic catalyst present. Finally, an amine reaction product is present in an additional reactor wherein the DCP is decomposed. The total acidic materials then present are the unneutralized strong catalyst and the mild acid reaction product of the amine and the acid catalyst. The reaction product between the acidic catalyst, preferably sulfuric acid, and the amine, preferably ammonia, appears to have a co-catalytic effect in the environmental milieu although we do not wish to be bound to that observation. When only the strong catalyst is present a maximum of about 90% of the DCP in the feed can be efficiently converted to AMS before tar begins to form. But when a reduced quantity of sulfuric acid and the amine reaction product are present, over 95% of the DCP can be converted without significant loss in AMS selectivity. When sulfuric acid is reacted with ammonia the reaction product is ammonium hydrogen sulfate.

Therefore it can be thought that there are two separate invention aspects actually present here. Firstly, there is the increased yield and selectivity to CHP reaction products in the first portion of the cleavage reaction by utilizing, inter alia, additional recycle materials and a multiplicity of reactors. Secondly, the DCP prepared in the first reaction scheme of the decomposition of CHP is then selectively decomposed in an additional reactor to AMS, phenol and acetone with particular selectivity to AMS. Either of these reactions can be coupled with the known prior art synthetic procedures. It is preferred to combine both of the separate inventive steps disclosed in this particular application to form a new and highly efficient decomposition of CHP to final products of phenol, acetone and AMS.

SUMMARY OF THE INVENTION

In accordance with the invention, there is a method for the enhanced decomposition of cumene hydroperoxide by acidic catalyst to phenol and acetone which comprises decomposing cumene hydroperoxide in a nonisothermal manner in the presence of excess acetone whereby the molar ratio of phenol to the acetone in a decomposition reactor is from about 1.1:1 to 1.5:1.

A further aspect of the invention is a method for enhancing the specify of the decomposition of dicumyl peroxide to alpha methylstyrene in the presence of an acidic catalyst which comprises carrying out the decomposition at a temperature of from about 80° to 110° C.

A further aspect of the invention is a method for carrying out the decomposition of dicumyl peroxide with an acidic catalyst which comprises performing such decomposition in the presence of the reaction product of (1) an amine with (2) an acidic material which can catalyze the decomposition of CHP.

A still further aspect of the invention is a composition comprising cumene, acidic catalyst for decomposition of CHP, dicumyl peroxide, dimethylbenzyl alcohol, phenol and acetone wherein the acetone is in a molar ratio to phenol of from about 1.1:1 to 1.5:1.

An additional aspect of the invention is a composition comprising cumene, acidic catalyst for decomposing CHP, DCP, water, phenol, acetone and a reaction product of (1) an amine with (2) an acid which catalyzes the decomposition of CHP.

A further aspect of the invention is a method for preparing phenol and acetone from the decomposition of CHP with an acidic catalyst which comprises (a) decomposing CHP at a specific acidic catalyst concentration and temperature thereby forming a composition comprising phenol, acetone and dicumyl peroxide, (b) transferring dicumyl peroxide to a plugged flow reactor wherein decomposition of dicumyl peroxide to phenol, acetone and AMS occurs in a weaker acidic catalyst medium and a higher temperature than in step (a).

A further aspect of the invention is a method for maintaining the control of an acid catalyzed CHP decomposition in a multiplicity of sequential reactors which comprises passing a portion of the outlet stream of the last sequential reactor into a reactor of plug flow design and a smaller size compared to the CHP decomposition reactors wherein the delta T° C. of the inlet temperature and the outlet temperature of said plug flow reactor is from about 4° to 16° C.

Another aspect of the invention is a method for enhancing the decomposition of CHP and producing CHP decomposition products therefrom which comprises recycling the CHP decomposition products to a CHP feedstream in the quantity of from about 10–25 times the weight of the CHP feedstream.

A further aspect of the invention is a method for enhancing the decomposition of CHP to phenol and acetone which comprises having additional water in the CHP decomposition reactor.

A CHP decomposition mass having an acetone to phenol molar ratio of about 1.1:1 to 1.5:1.

DETAILED DESCRIPTION OF INVENTION

Figure 1:
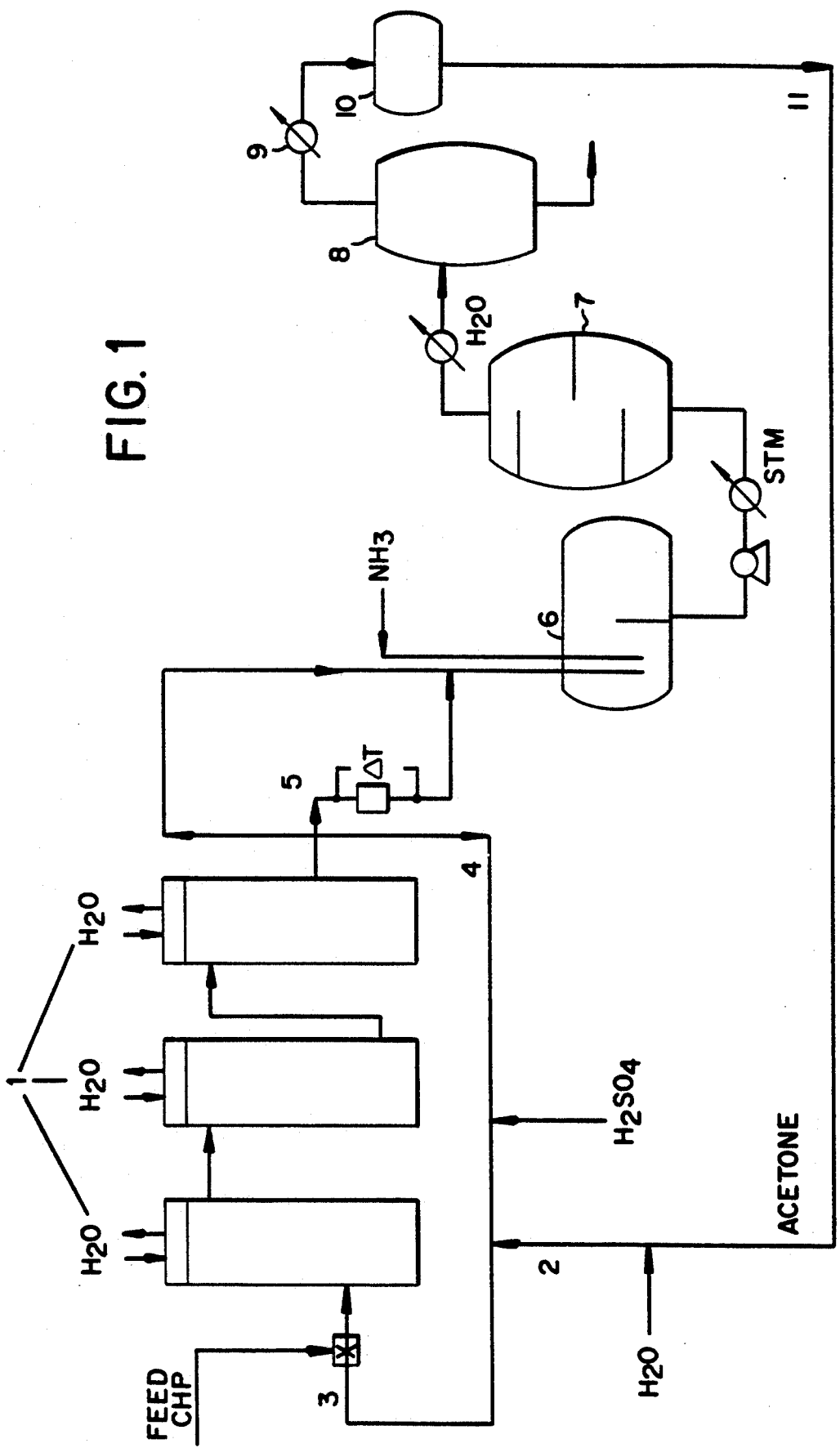

The cleavage reaction in the manufacture of phenol and acetone from cumene is well known. In the manufacturing scheme, a feed stream of cumene is oxidized to cumene hydroperoxide. It is then passed into a cleavage unit wherein an acid catalyst is added and the CHP is then decomposed to phenol, acetone and other by-products. The acidic catalyst employed can be any acidic material. Generally, since corrosion can be a factor, the heavily corrosive inorganic acids such as hydrochloric and hydrobromic are not employed. Certain acids such as phosphoric, sulfuric and $SO_2$ can be employed. Generally sulfuric acid is preferred in this particular reaction as a catalyst.

The CHP decomposition reaction is known to be extremely fast and because of its heavily exothermic nature is carried out over a short time period and essentially to completion in most processes. In fact it is common to use a constant boiling or refluxing type system for the isothermal cleavage reaction. This is generally the constant boiling temperature of the CHP feed stream and product mixture present in the cleavage reactor at a given moment. Generally this can vary from about 70° to 90° C. Since this is the general CHP feed stream as well as the reactant product, the phenol to acetone molar ratio is essentially 1 to 1 throughout the course of the reaction.

It has now been found that a recycle of acetone to the cleavage vessel(s) is quite helpful in increasing the overall efficiency, selectivity and yield of the cleavage reaction. A molar ratio of about 1.1 to 1.5 to 1 (acetone to phenol), preferably 1.15 to 1.4 to 1, should be maintained in the cleavage vessel(s). This additional acetone has a tendency to reduce the rate of the decomposition reaction of CHP thereby making it more controllable and more selective. In fact the CHP decomposition reaction is carried out in a non-isothermal manner in accordance with this invention.

In addition it has also been found that additional cumene should also be present in the reactor thereby providing a better controlled reaction. This quantity of cumene should be from about 1 to about 20 weight percent of the cleavage reactor composition preferably about 10 to 18%. As previously mentioned it is preferred to run the initial cleavage reaction in a multiplicity of reactors in sequence. Generally the temperature can vary from about 45° C. to about 74° C. Pressure is not unduly significant with respect to the chemistry. However in order to overcome the resistance of the system and prevent evaporation of acetone, pressure can vary from about one atmosphere to five atmospheres. These reactors are generally shell-in-tube heat exchangers and a specific heat exchange surface not less than 30 to 35 meter$^2$ per metric ton of 100% CHP per hour. It is most preferred to have CHP conversion in a three reactor sequence preferably having 30 to 60% in the first, 25 to 50% in the second and 30 to 10% in the third. The acetone fed to the reactors is on the basis of one metric ton of technical CHP according to the algorithm $$G_{acetone} = G_{CHP} \times 0.17([CHP]) + \frac{40}{G_{CHP}[CHP]}.$$

wherein:
G acetone is quantity of fed acetone, metric ton/hour,
GCHP is quantity of technical CHP fed to the unit, metric ton/hour,
[CHP] is concentration in technical CHP, weight %/100.

The temperature of the reactions among the three sequentially placed reactors are about 50° to 62° C. first, about 62° to 57° C. second, and about 57° to 50° C. third. These temperatures are below the constant boiling temperature of the CHP decomposition mass thereby decomposing the CHP in a non-isothermal manner. It is preferred to have the reactors controlled by a plug-flow mini-reactor which is located by-pass after the third sequential reactor and through which a portion of the products emitted from the last sequential reactor passes. This mini-reactor has a product residence time of generally not more than 3 minutes with a measurement of temperature difference at the inlet and outlet ($\Delta T$), of the mini-reactor maintained at about 4° to 16° C., preferably 5° to 15° C. This mini-reactor helps to produce products of optimal composition. Its primary function is to decompose essentially all of the CHP remaining in the effluent passed through the mini-reactor so as to be an analytical indication of the completeness of the CHP decomposition reaction.

The quantity of catalyst which is present can vary substantially. The catalyst quantity is generally from about 50 to about 750 parts per million of the reactor composition, preferably about 150 to 600 ppm. The reaction is of relatively short duration throughout the sequential reactors. Generally anywhere from about 30 seconds to about 3 minutes is appropriate. However optimal conditions when coupled with other optimized parameters are from about 45 seconds to 2 minutes. One of the significant parameters is the quantity of CHP decomposition product produced in these sequential reactors which is recycled to the CHP feed stream. This recycle stream can vary in amount from about 10 to 25 times the mass flow of the CHP feed stream. Not only does this recycle bring about higher selectivity but it also provides a significant safety factor to the process.

Another factor is the presence of additional water in the CHP decomposition reactors. This is water above the usual amount of water produced in the CHP decomposition reaction. Such water can initially be added in the recycle stream. The level of water in the decomposition reactors should not be higher than 3 wt. % of the CHP decomposition mass, preferably no greater than 2 wt. % and is most preferably in the range of 0.8 to 1.2 wt. %.

In this reaction CHP is decomposed to phenol and acetone while DMBA and CHP react to form DCP and water. While the prior art in this situation at best removes the product stream to a second or even third reactor as shown in U.S. Pat. No. 4,356,618 with no change in catalyst concentration, the catalyst system in this invention is now altered. Such alteration can be made by adding any type of basic compound thereby partially neutralizing the acid present from the CHP decomposition. It has been found that it is preferred to utilize an amine to reduce the acid concentration, particularly where the acid is sulfuric acid. Examples of such amines include hydrazine, ammonia, alkyl amines of one to five carbon atoms and the like. It is preferred to use ammonia particularly where the catalyst is sulfuric acid. Generally the ammonia is added as aqueous ammonia of relatively low concentration, from about 0.15 to 10 wt. % ammonia. Generally about 10 to 99 wt. % of the original acid catalyst is neutralized, preferably the quantity of catalyst neutralized is from about 30 to about 70 wt. %. When $H_2SO_4$ is employed as the catalyst or when a specific catalyst such as $SO_2$ or $SO_3$ which can react with water present in the reactor and thereby form a sulfurous or sulfuric acid is present, it is preferred to use ammonia as the material to react with the sulfurous or sulfuric acid. The reaction product is the weakly acidic salt ammonium hydrogen sulfate. In this particular case it is believed that the ammonium hydrogen sulfate functions as a co-catalyst. The formation of this additional weakly acidic material as well as the reduced concentration of the original acid catalyst bringing about the CHP decomposition, particularly sulfuric acid, appears to provide a much better controlled decomposition of DCP to phenol, acetone and AMS thereby maximizing useful products and minimizing side products such as AMS dimers and tar. As will be shown in the following specific examples of this invention, there is a selective and efficient preparation of AMS, phenol and acetone from DCP decomposition through the usage of a much lower temperature and the reduced catalyst concentration from the initial CHP decomposition catalyst in comparison to the U.S. Pat. No. 4,358,618 temperature range of approximately 120° to 150° C. and an unchanged catalyst concentration. Generally rally the invention temperature range is 80°–110° C., preferably from about 85° to 105° C. for a period of about 20 to about 60 minutes at a pressure range from about 0.3 to 5 atmospheres.

Following this particular reaction there can be a cooling of the cleavage products by evaporation of acetone in a separate vessel. The evaporated acetone condenses under vacuum for example, 0.25 to about 0.9 of one atmosphere and an operating temperature of about 80°–110° C. and at least a portion, preferably all of that is returned to the CHP decomposition reactor sequence. Generation of at least a portion of the recycle acetone in this manner decreases overall plant energy usage through the more efficient usage of steam, utilizes equipment more efficiently and debottlenecks equipment. Additionally, the water concentration in the recycling acetone can be more accurately controlled since the overall cleavage product is constant in composition and the quantity of water present in the evaporator overhead stream, recycle acetone, is a function of the operating temperature and pressure of the evaporator vapor-liquid equilibrium. As long as the temperature and pressure are held constant, the water concentration of the, overhead vapor remains constant and self-controlling.

FIGURE 1

The reaction sequence scheme for the decomposition of CHP including the preparation of DCP and subsequent decomposition to phenol, acetone and AMS.

With reference to the descriptive drawing it should be noted that the specific ranges or numbers are in relationship to a specific embodiment of carrying out the invention. They are not intended to unreasonably restrict the broad nature of the invention in any manner.

Cumene is oxidized to CHP. The stream of CHP primarily having cumene hydroperoxide therein but also containing DMBA, acetophenone, and various organic acids as well as other materials is brought to a cleavage reactor having a sulfuric acid catalyst in the quantity of about 250 parts per million of sulfuric acid per weight of composition mass. This CHP decomposition and process is conducted in 1 to 2 minutes in 3 sequentially installed reactors of the shell and tube heat exchangers as shown at 1. These reactors have a specific surface not less than about 30 to 35 meter squared per ton of 100% CHP per hour. CHP conversion in the reactors in one pass is 30 to 35%, 30 to 40%, 30 to 15%, respectively. While in the cleavage reactor the mole ratio of acetone to phenol is maintained at 1.5 to 1. As shown by the feed line, 2, the acetone is fed to mixer, 3, in line prior to the first CHP decomposition reactor. The amount of fed acetone when CHP flow rate is decreased is increased to a higher ratio of acetone to phenol. The circulation ratio of CHP cleavage products to CHP feedstream on a weight basis through the 3 sequentially installed reactors is 20 to 1, see reaction circulation loop, 4. The three decomposition temperatures in the sequential reactors are respectively 50° to 62° C., 62° to 57° C., and 57° to 50° C., respectively. Following the third sequential reactor, is a plug-flow mini-reactor, 5. This mini-reactor funtions as a calorimeter with respect to the three sequentially placed reactors. Only a small portion of the effluent of the reactor passes through this mini-reactor. The term mini only refers to the size of the unit in comparison to the three previous reactors. This plug-flow mini-reactor has a product residence time of generally not more than 3 minutes and with a measurement of temperature difference at the inlet and outlet of the mini-reactor maintained at about 5° to 15° C. Following exiting from the last decomposition reactor, 1, an aqueous ammonia solution is introduced into the cleavage products at a weight ratio of sulfuric acid (catalyst) to ammonia of (11-23:1) in holding tank, 6. In this tank CHP level is brought to a minimum, preferably zero, and the ammonium bisulfate generated. Cleavage products are then transferred to plug-flow reactor, 7, and maintained at a temperature of 85° to 95° C. and a pressure of 0.3 to about 0.5 atmosphere above normal atmospheric pressure for a period of about 25 to 45 minutes. In this tank the DCP is decomposed to phenol, AMS and acetone. Thereafter the pressure is lowered to about 0.35 to 0.45 of one atmosphere pressure thereby providing coolage of the cleavage products through the evaporating of the acetone by use of evaporator vessel, 8. The vaporized acetone passes overhead in the evaporator and is subsequently condensed in condenser, 9, collected in vessel, 10, and then pumped to reaction circulation loop, 4, via pump, 11.

Below are specific examples of the invention. These examples are not intended to limit the invention but are intented illustratively to exemplify the invention. The results of the examples demonstrate the increased effectiveness of the inventive processes.

EXAMPLES 1-4

Decomposition of technical CHP containing cumene 12.16 wt. %, acetophenone 0.40 wt. %, DMBA 3.64 wt. %, CHP 83.80 wt. % was conducted an installation similar to that shown in FIG. 1. It was conducted in equimolar mixture of phenol and acetone containing 0.03 wt. % of $H_2SO_4$ and additionally introduced acetone in amount of 14.96 wt. % relatively on the basis of fed technical CHP. The temperature in each of three sequentially installed reactors was maintained non-isothermal in a range of 50°-62° C., 62°-57° C., 57°-50° C., respectively with a pressure of about 1 to 5 atmospheres. Product recycle circulation weight ratio was 17 to 1. Flow mixing and mini-reactor for T measurement were installed in the scheme. The delta T value was 9° C. CHP decomposition time was 2 minutes.

Aqueous ammonia solution was introduced into plug-flow reactor in amount which is necessary to translate 50% weight of $H_2SO_4$ into $NH_4HSO_4$. The temperature in DCP plug-flow reactor was maintained at 93° C., pressure 1.5 atm. Product residence time in the plug-flow reactor was varied from 35 min. to 60 min.

Data for DCP content and yield of AMS of different examples are given in Table 1.

After distilling of additionally fed acetone the following was found in 100 grams of produced product of Example 4 (Table 1): cumene -12.16,AP-0.4 g, DMBA- 0.1 g, AMS-2.53 g, DCP-0.05 g, AMS dimer-0.37 g, complex ethers-0.30 g. The sum of by-products which are component of phenol tar (AP+DMBA+DCP+AMS Dimer +CP) was 1.22 g.

TABLE 1

| Example | Reaction Temperature °C. | Time in plug flow reactor min. | DCP concentration in cleavage products wt. % | Yield of AMS mole % |
|---|---|---|---|---|
| 1 | 93 | 25 | 0.4 | 78.0 |
| 2 | 93 | 35 | 0.2 | 81.0 |
| 3 | 93 | 45 | 0.1 | 80.5 |
| 4 | 93 | 60 | 0.05 | 80.0 |

The given examples demonstrate the stability of AMS yield at various product residence time in plug-flow reactor and various DCP conversion.

EXAMPLE 5-6

Decomposition of technical CHP of the same composition position as in Examples 1-4 was carried out with preliminary mixing and without preliminary mixing of technical CHP and recycled products in a Venturi type motionless mixer.

TABLE 2

| CHP conversion, % | | 25 | 50 | 75 | 90 |
|---|---|---|---|---|---|
| relative rate of CHP decomposition | without mixing | 1 | 1 | 1 | 1 |
| | with mixing | 1.19 | 1.21 | 1.18 | 1.22 |

The given examples demonstrate the increase of CHP decomposition rate in case of preliminary good mixing of CHP and its cleavage products up by 20% relatively in comparison with examples without preliminary mixing.

EXAMPLE 7-12

Decomposition of technical CHP of the same composition as in example 1-4 was conducted with preliminary mixing of recycled product flow and technical CHP the same conditions as in examples 1-4 and various value of temperature difference (delta T) at the inlet and outlet of mini-reactor.

TABLE 3

| EX | Mini reactor Delta T value °C. | Mole ratio Ac/Ph | CHP conversion in reactors 1 | 2 | 3 | Yield of AMS mole % |
|---|---|---|---|---|---|---|
| 7 | 0 | 1:1 | 100 | — | — | 52.0 |
| 8 | 3 | 1.05:1 | 80 | 20 | — | 60.0 |
| 9 | 5 | 1.15:1 | 60 | 30 | 10 | 76.0 |
| 10 | 9 | 1.5:1 | 35 | 40 | 15 | 80.0 |
| 11 | 15 | 1.5:1 | 30 | 40 | 10 | 75.0 |
| 12 | 17 | 1.6:1 | 34 | 30 | 10 | |

Examples 9–11 demonstrate the production of good results as shown by the yield of AMS at various ranges of CHP conversions in one pass in three sequentially installed reactors wherein acetone is additionally fed and mole ratio acetone/phenol of 1.15–1.5 is maintained. The delta T values varies dependent upon the unreacted CHP remaining in the flow through the mini-reactor.

Example 7 demonstrates the low yield of AMS without acetone introduction into CHP decomposition reactors. The delta T value of 0° C. shows that the CHP is depleted.

Example 12 illustrates the influence of acetone fed to CHP decomposition unit above the preferred molar ratio. The high delta T value at the mini-reactor reflects the presence of significant levels of nonconverted CHP in the flow to the mini-reactor. Such levels of CHP can be a safety issue.

EXAMPLES 13-17

Decomposition of technical CHP of the same composition as in Ex. 1–4 was conducted under the same conditions as in Ex. 1–4 and various value of degree of $H_2SO_4$ conversion to $NH_4HSO_4$. There was obtained a certain yield of desired products after stripping stage of acetone additionally fed to CHP decomposition unit.

| EX | Degree of $H_2SO_4$ conversion to $NH_4HSO_4$, % | Concentration of $H_2SO_4$ in cleavage prod. % weight | Concentration of $NH_4HSO_4$ in cleavage prod. % weight | Yield of AMS, mole % before acetone stripping | after acetone stripping |
|---|---|---|---|---|---|
| 13 | 0 | 0.027 | 0 | 74 | 52 |
| 14 | 25 | 0.020 | 0.0082 | 78 | 58 |
| 15 | 50 | 0.0136 | 0.0158 | 80 | 78 |
| 16 | 75 | 0.0082 | 0.0221 | 82 | 79.6 |
| 17 | 100 | 0 | 0.030 | 82 | 82 |

EXAMPLE 18 (COMPARATIVE)

Decomposition of technical CHP of the same composition as in example 1–4 was conducted in the same installation as Examples 1–4 but without preliminary flow mixing, without introduction of extra acetone quantity to CHP decomposition unit, i.e. in equimolar acetone-phenol mixture. Aqueous ammonia solution was not fed to plug-flow reactor wherein the temperature was maintained at 93° C. CHP conversion in three sequentially installed reactors was 80, 20, and 0% respectively. Delta T value was 0° C.

The following was found in 100% of produced cleavage products analyzed after plug-flow reactor as shown at 7 of FIG. 1. cumene-12.16 g, AP-0.6 g, DMBA-0.10 g, AMS-1.64 g, DCP-0.01 g, cumylphenols (CP)-1.25 g, AMS dimer -1.0 g.

The yield of AMS was 52 mol.% on the basis of DMBA present in the technical CHP (compare to 75–80 mole% in Examples 9-11). The sum of by-product which were components of phenol tar (AP+DMBA+DCP+CP+AMS dimer) was 2.96 g (compare to 1.22 g of Examples 1–4). The high level of phenol tar is evidence that some of the CHP is actually converted to additional DMBA under the comparative example process conditions. Additional yield loss arises from such conversion.

What is claimed is:

1. An improved method for the decomposition of cumene hydroperoxide by acidic catalyst to phenol and acetone wherein the improvement comprises decomposing cumene hydroperoxide in a non-isothermal manner in the presence of excess acetone whereby the molar ratio of acetone to phenol in a decomposition reactor is from about 1.1:1 to 1.5:1 whereby the rate of decomposition of cumene hydroperoxide is reduced and the reaction is more controllable and more selective.

2. The method in accordance with claim 1 wherein the acetone is thoroughly mixed with the cumene hydroperoxide feed-stream.

3. The method in accordance with claim 1 wherein the excess acetone is added in accordance with the algorithm $$G\ acetone = G_{chp}(0.17)([CHP]) + 40/(G_{chp}[HP])$$

where G acetone is quantity of fed acetone, metric ton/hour; $G_{chp}$ is quantity of technical cumene hydroperoxide fed to the unit, metric ton/hour; and [CHP] is concentration in technical cumene hydroperoxide, weight %/100.

4. The method in accordance with claim 1 wherein the cumene hydroperoxide is decomposed in a multiplicity of separate sequential reactors each with a controlled temperature range.

5. The method in accordance with claim 4 wherein a first reactor is operated in a temperature range of about 50° to 62° C. a second reactor in a temperature range of about 62° to 57° C. and the third and last reactor in a temperature range of about 57° to 50° C.

6. The method in accordance with claim 4 wherein portions of the outlet stream of the last sequential reactor is passed into a reactor of plug flow design and smaller size compared to the decomposition reactor wherein the delta T°C. of the inlet temperature and outlet temperature of said plug flow reactor is from about 4° to 16° C.

7. The method in accordance with claim 1 wherein the acidic catalyst is sulphuric acid.

8. The method in accordance with claim 1 wherein the catalyst is in a concentration of from about 150 to 500 ppm of the weight of cumene hydroperoxide decomposition product.

9. The method in accordance with claim 1 wherein the temperature of the cumene hydroperoxide decomposition is about 45° to 75° C.

10. The method in accordance with claim 1 wherein the quantity of cumene hydroperoxide remaining after decomposition is from about 0.3 to 1.5 wt. % of the total weight of the decomposition products.

11. An improved method for the decomposition of dicumyl peroxide to alpha methylstyrene in the presence of an acidic catalyst wherein the improvement comprises carrying out the decomposition at a temperature of from about 80° to 110° C. whereby selectivity is enhanced.

12. The method in accordance with claim 11 wherein the acid catalyst comprises a reaction product of an amine and an acidic catalyst used to catalyze the decomposition of cumene hydroperoxide.

13. The method in accordance with claim 12 wherein the acidic catalyst used to decompose cumene hydroperoxide is sulphuric acid.

14. The method in accordance with claim 12 wherein the amine is ammonia.

15. The method in accordance with claim 14 wherein the acid reaction product is ammonium hydrogen sulfate.

16. An improved method for carrying out the decomposition of dicumyl peroxide with an acidic catalyst system wherein the improvement comprises performing such decomposition in the presence of the reaction product of (1) an acidic material which can catalyze the decomposition of cumene hydroperoxide with (2) an amine suitable for partially neutralizing the acidic materials whereby a weakly acid material is formed and the decomposition is better controlled.

17. A method in accordance with claim 16 wherein the acidic material is sulphuric acid.

18. A method in accordance with claim 16 wherein the amine is ammonia.

19. A method in accordance with claim 17 wherein the amine is ammonia.

20. A method in accordance with claim 16 wherein the reaction is carried out at a temperature of from about 80° to 110° C.

21. A composition comprising cumene hydroperoxide, cumene, acidic catalyst for decomposition of cumene, dicumyl peroxide, dimethylbenzyl alcohol, phenol, and acetone wherein the acetone is in a molar ratio to phenol of from about 1.1:1 to 1.5:1.

22. A composition comprising cumene, acidic catalyst for decomposing cumene hydroperoxide, dicumyl peroxide, water, phenol, acetone and a reaction product of (1) an amine with (2) an acid which catalyzes the decomposition cumene hydroperoxide.

23. A composition in accordance with claim 22 wherein the acidic catalyst is sulphuric acid.

24. A composition in accordance with claim 22 wherein the amine is ammonia.

25. A composition in accordance with claim 23 wherein the amine is ammonia.

26. A composition in accordance with claim 25 wherein a reaction product is ammonium hydrogen sulfate.

27. An improved method for preparing phenol and acetone from the decomposition of cumene hydroperoxide with an acidic catalyst wherein the improvement comprises (a) decomposing cumene hydroperoxide at a specific acidic catalyst concentration and temperature whereby a composition comprising phenol, acetone and dicumyl peroxide is formed, (b) transferring dicumyl peroxide to a plug flow reactor wherein decomposition of dicumyl peroxide to phenol, acetone and alphamethylstyrene occurs in a weaker acidic catalyst medium and a higher temperature than the catalyst concentration and temperature in step (a) whereby the dicumyl peroxide decomposition is better controlled.

28. The method in accordance with claim 27 wherein in step (a) the temperature is from about 70°-90° C. and the catalyst concentration is from about 50–750 ppm of the decomposition mass and in step (b) the temperature is from about 80° to 110° C. and the catalyst in step (a) has been lowered about 10 to 99 mole %.

29. The method in accordance with claim 27 wherein at least a portion of the lowering of the acid concentration of (a) is accomplished through the addition of an amine.

30. An improved method for maintaining control of an acid catalyzed cumene hydroperoxide decomposition in a multiplicity of sequential reactors wherein the improvement comprises passing a portion of the outlet stream of the last sequential reactor into a reactor of plug flow design and a smaller size compared to the cumene hydroperoxide decomposition reactors wherein the delta T°C. of the inlet temperature and the outlet temperature of said plug flow reactor is from about 4° to 16° C. whereby the smaller size reactor decomposes essentially all of the cumene hydroperoxide remaining in said portion of the outlet stream and provides an analytical indication of the completeness of the cumene hydroperoxide decomposition reaction and the reactors are thereby controlled.

31. The method in accordance with claim 30 wherein the delta T°C. is from about 5° to 15° C.

32. An improved method for enhancing the decomposition of cumene hydroperoxide and producing cumene hydroperoxide decomposition products therefrom wherein the improvement comprises recycling the cumene hydroperoxide decomposition products to a cumene hydroperoxide feedstream in the quantity of from about 10–25 times the weight of the cumene hydroperoxide feedstream whereby selectivity is higher and safety of the process is improved.

33. The method in accordance with claim 32 wherein additional acetone is added to the cumene hydroperoxide decomposition products as to maintain a ratio of about 1.1 to 1 to 1.5 to 1 acetone to phenol in the cumene hydroperoxide decomposition reaction.

34. The method in accordance with claim 33 wherein additional water is added to the cumene hydroperoxide decomposition products to a level not greater than 3 wt. % in the cumene hydroperoxide decomposition mass.

35. The method in accordance with claim 34 wherein the level is not greater than 2 wt. %.

36. The method in accordance with claim 35 wherein the level is not greater than 1.5 wt. %.

37. An improved method for enhancing the decomposition of cumene hydroperoxide to phenol and acetone wherein the improvement comprises introducing additional water into the cumene hydroperoxide decomposition reactor.

38. A cumene hydroperoxide decomposition mass produced from the reaction of cumene hydroperoxide with an acid catalyst in a non-isothermal manner having an acetone to phenol mole ratio of about 1.1 to 1 to 1.5 to 1.

39. A method for the efficient generation of recycle acetone in a process which prepares phenol and acetone from cumene comprising
(a) decomposing dicumylperoxide to phenol, acetone, and alpha methyl styrene
(b) feeding at least a portion of decomposition products of (a) to a separate vessel wherein operating temperature is higher operating pressure is lower than in step (a), thereby allowing acetone to evaporate,
(c) sending at least a portion of acetone collected from step (b) to the cumene hydroperoxide decomposition reaction.

* * * * *